(12) United States Patent
Yoshinaka et al.

(10) Patent No.: US 8,067,517 B2
(45) Date of Patent: Nov. 29, 2011

(54) WATER-SOLUBLE COPOLYMER HAVING ALKYL-MODIFIED CARBOXYL GROUPS

(75) Inventors: Masatoyo Yoshinaka, Himeji (JP); Shinji Kobayashi, Himeji (JP); Yuichiro Moritmitsu, Himeji (JP)

(73) Assignee: Sumitomo Seika Chemicals Co., Ltd., Kako-gun, Hyogo (JP)

( * ) Notice: Subject to any disclaimer, the term of this patent is extended or adjusted under 35 U.S.C. 154(b) by 245 days.

(21) Appl. No.: 12/094,327

(22) PCT Filed: Nov. 13, 2006

(86) PCT No.: PCT/JP2006/322557
§ 371 (c)(1),
(2), (4) Date: May 20, 2008

(87) PCT Pub. No.: WO2007/058143
PCT Pub. Date: May 24, 2007

(65) Prior Publication Data
US 2009/0292078 A1    Nov. 26, 2009

(30) Foreign Application Priority Data

Nov. 21, 2005 (JP) ................. 2005-335628

(51) Int. Cl.
C08F 220/06 (2006.01)
C08F 220/18 (2006.01)
(52) U.S. Cl. ............... 526/328.5; 526/317.1; 526/318.4; 526/319; 526/328
(58) Field of Classification Search ............... 526/317.1, 526/318.4, 319, 328, 328.5
See application file for complete search history.

(56) References Cited

U.S. PATENT DOCUMENTS

| | | | |
|---|---|---|---|
| 3,915,921 A * | 10/1975 | Schlatzer, Jr. | 526/238.23 |
| 3,940,351 A * | 2/1976 | Schlatzer, Jr. | 524/795 |
| 4,066,583 A * | 1/1978 | Spaulding | 526/238.23 |
| 4,190,562 A * | 2/1980 | Westerman | 526/238.23 |
| 4,509,949 A * | 4/1985 | Huang et al. | 8/558 |
| 5,004,598 A | 4/1991 | Lochhead et al. | |
| 5,021,525 A * | 6/1991 | Montague et al. | 526/210 |
| 2005/0159571 A1* | 7/2005 | Hamamoto et al. | 526/317.1 |

FOREIGN PATENT DOCUMENTS

| | | |
|---|---|---|
| EP | 0128237 A1 | 12/1984 |
| EP | 0328725 A2 | 8/1989 |
| EP | 0709406 A1 | 5/1996 |
| EP | 0 739 912 A2 | 10/1996 |
| EP | 1 489 114 A1 | 12/2004 |
| EP | 1 772 470 A1 | 4/2007 |
| JP | 57-174306 A | 10/1982 |
| JP | 4-39312 A | 2/1992 |
| JP | 2001-181123 A | 7/2001 |
| JP | 2003-268009 A | 9/2003 |
| JP | 2004-281055 A | 10/2004 |
| JP | 2005-126455 A | 5/2005 |
| JP | 2006-036910 A | 2/2006 |
| WO | 03/016382 A1 | 2/2003 |

OTHER PUBLICATIONS

Supplementary European Search Report dated Jan. 18, 2010, issued in corresponding European Patent Application No. 06823330.3.
International Search Report of PCT/JP2006/322557; date of mailing Jan. 30, 2007.
European Search Report dated Jun. 3, 2009, issued in corresponding European Patent Application No. 06823331.1.
Notification of Transmittal of Translation of the International Preliminary Report on Patentability (Form PCT/IB/338) of International Application No. PCT/JP2006/322557 mailed Jun. 5, 2008 with Forms PCT/IB/373, PCT/IB/326, PCT/ISA/237 and English translation of form PCT/ISA/237.
International Search Report of PCT/JP2006/322556, date of mailing Jan. 30, 2007.
Notification of Transmittal of Translation of the International Preliminary Report on Patentability (Form PCT/IB/338) of International Application No. PCT/JP2006/322556 mailed May 22, 2008 with Forms PCT/IB/373, PCT/IB/236 PCT/ISA/237 and English translation of form PCT/ISA/237.
European Office Action issued Jul. 16, 2010, issued in corresponding European Patent Application No. 06823331.1-2109.

* cited by examiner

*Primary Examiner* — David W Wu
*Assistant Examiner* — Vu A Nguyen
(74) *Attorney, Agent, or Firm* — Westerman, Hattori, Daniels & Adrian, LLP

(57) ABSTRACT

A water-soluble copolymer having alkyl-modified carboxyl groups which is able to produce a neutralized viscous liquid in which although its viscosity is very low when no electrolyte exists, the viscosity greatly increases when electrolytes are added, which has a sufficiently high viscosity and a very high transmittance and which has moist textures without stickiness even in the presence of a relatively high concentration of electrolytes, and a thickening agent comprising the same.

6 Claims, No Drawings

WATER-SOLUBLE COPOLYMER HAVING ALKYL-MODIFIED CARBOXYL GROUPS

TECHNICAL FIELD

The present invention relates to a water-soluble copolymer having alkyl-modified carboxyl groups. More specifically, the present invention relates to a water-soluble copolymer having alkyl-modified carboxyl groups, which may be preferably used as a thickening agent for cosmetics and the like.

BACKGROUND

A variety of copolymers are known as copolymers of (meth)acrylic acid and alkyl(meth)acrylate, which are used in thickening agents for cosmetics and the like; moisturizers for cataplasms and the like; emulsifiers; suspension stabilizers for suspensions; and the like. For example, a copolymer obtained by reacting a specific amount of olefin-based unsaturated carboxylic acid monomers and a specific amount of alkyl(meth)acrylate (a carbon number of the alkyl group is 10-30) (See Patent Document 1), a copolymer obtained by reacting a specific amount of olefin-based unsaturated carboxylic acid monomers and a specific amount of alkyl(meth)acrylate (a carbon number of the alkyl group is 10-30) and a cross linking agent (See Patent Document 2), a copolymer obtained by reacting olefin-based unsaturated carboxylic acid monomers and alkyl (meth)acrylate (a carbon number of the alkyl group is 8-30) (See Patent Document 3) and the like are known.

These copolymers of (meth)acrylic acid and alkyl(meth)acrylate are used in the above applications usually after dissolving into water and the like and neutralize with alkali to form a neutralized viscous liquid at a concentration of about 0.1 to 1 weight %.

This neutralized viscous liquid had a problem that their viscosity or transmittance reduces and a part of the copolymer precipitates when electrolytes used as various raw materials for products or additives coexist even at relatively low concentrations.

In particular, recently, in a field of cosmetics and the like, cosmetics containing high amounts of minerals and the like in order to differentiate from other products as well as various properties, for example, good appearances such as transparency, non-sticky texture and the like are in the spotlight. Therefore, it is desired to invent a thickening agent which can form a neutralized viscous liquid having a high viscosity and a high transmittance even in the presence of a relatively high concentration of electrolytes.

[Patent Document 1] JP 6190/1976A
[Patent Document 2] JP 232107/1984A
[Patent Document 3] U.S. Pat. No. 5,004,598

DISCLOSURE OF THE INVENTION

The object of the present invention is to provide a water-soluble copolymer having alkyl-modified carboxyl groups which is able to produce a neutralized viscous liquid which has a sufficiently high viscosity and a very high transmittance and which has moist textures without stickiness even in the presence of a relatively high concentration of electrolytes, and a thickening agent containing the same.

The present invention relates to, as will be described, water-soluble copolymer having alkyl-modified carboxyl groups.

(1) A water-soluble copolymer having alkyl-modified carboxyl groups which is obtained by polymerizing 100 parts by weight of (meth)acrylic acid, 5-10 parts by weight of lauryl (meth)acrylate, and 0-0.1 parts by weight of a compound having two or more of ethylenic unsaturated groups, wherein a 1 weight %-neutralized viscous liquid shows a viscosity of 1000 mPa·s or lower and a transmittance of 95% or higher, and when 1-7 parts by weight of sodium chloride is added to 100 parts by weight of the neutralized viscous liquid, the liquid shows a highest viscosity of 10000-30000 mPa·s and a transmittance of 95% or higher.

(2) The water-soluble copolymer having alkyl-modified carboxyl groups according to (1), wherein the compound having two or more of ethylenic unsaturated groups is at least one selected from a group consisting of pentaerythritol allyl ether, diethylene glycol diallyl ether, polyethylene glycol diallyl ether and polyallyl saccharose.

(3) A thickening agent comprising the water-soluble copolymer having alkyl-modified carboxyl groups according to (1) or (2).

The present invention will be explained in detail as below.

Additionally, in the present invention, acrylic acid and methacrylic acid are inclusively described as (meth)acrylic acid.

Further, in the present invention, neutralization for the neutralized viscous liquid is to make the pH of the liquid 6.5-7.5.

In the present invention, the water-soluble copolymer having alkyl-modified carboxyl groups is obtained by polymerizing (meth)acrylic acid and lauryl(meth)acrylate and optionally a compound having two or more of ethylenic unsaturated groups.

When (meth)acrylic acid and lauryl(meth)acrylate are combined in the present invention, either or both of (meth)acrylic acid and lauryl(meth)acrylate may be used alone or in a combination of two or more, respectively. Among these combinations, a combination of acrylic acid and lauryl methacrylate is preferably used because they are easily treated due to liquid at room temperature and viscosity properties and transmittances are excellent regarding neutralized viscous liquids of the water-soluble copolymer having alkyl-modified carboxyl groups obtained therefrom and the liquids in the presence of electrolytes.

The amount of lauryl(meth)acrylate used in the present invention is 5-10 parts by weight, more preferably 6-9.1 parts by weight with respect to 100 parts by weight of (meth)acrylic acid. When the amount of lauryl(meth)acrylate is less than 5 parts by weight with respect to 100 parts by weight of (meth)acrylic acid, it is possible that a viscosity in the presence of electrolyte of a neutralized viscous liquid of the obtained water-soluble copolymer having alkyl-modified carboxyl groups is insufficient, while when the amount is more than 10 parts by weight, it is possible that water-solubility of the obtained water-soluble copolymer having alkyl-modified carboxyl groups deteriorates.

The compounds having two or more of ethylenic unsaturated groups optionally used in the present invention are not especially limited but compounds in which the ethylenic unsaturated groups are allyl groups are preferable. Among them, pentaerythritol allyl ether such as pentaerythritol diallyl ether, pentaerythritol triallyl ether, pentaerythritol tetraallyl ether and the like, diethylene glycol diallyl ether, polyethylene glycol diallyl ether and polyallyl saccharose are more preferable. These compounds having two or more of ethylenic unsaturated groups may be used alone or in combination of two or more of them.

The amount of the compound having two or more of ethylenic unsaturated groups used in the present invention is 0.001-0.1 parts by weight, more preferably 0.001-0.044 parts by weight with respect to 100 parts by weight of (meth)acrylic acid. When the amount of the compound having two or more of ethylenic unsaturated groups is more than 0.1 parts by weight, it is possible that a transmittance in the presence of electrolyte of a neutralized viscous liquid of the obtained water-soluble copolymer having alkyl-modified carboxyl groups deteriorates or the liquid becomes clouded.

In the present invention, a method for obtaining the water-soluble copolymer having alkyl-modified carboxyl groups by polymerizing (meth)acrylic acid and 5-10 parts by weight of lauryl(meth)acrylate with respect to 100 parts by weight of (meth)acrylic acid and optionally 0-0.1 parts by weight of a compound having two or more of ethylenic unsaturated groups with respect to 100 parts by weight of (meth)acrylic acid is not especially limited but ordinary methods such as a method for polymerizing these materials by stirring them in a solvent under an inactive gas atmosphere in the presence of a polymerization initiator and the like may be used.

Inactive gases for producing an inactive gas atmosphere include, for example, a nitrogen gas, an argon gas and the like.

The aforementioned solvent is not especially limited insofar as they dissolve (meth)acrylic acid, lauryl (meth)acrylate and a compound having two or more of ethylenic unsaturated groups but not the obtained water-soluble copolymer having alkyl-modified carboxyl groups and do not inhibit a polymerization reaction.

Examples of such a solvent include, for example, normal pentane, normal hexane, normal heptane, cyclopentane, cyclohexane and the like. Among them, normal hexane and normal heptane are preferably used.

The amount of the solvent to be used is preferably 300-5000 parts by weight with respect to 100 parts by weight of (meth)acrylic acid from viewpoints of improving stirring workability and economy.

The aforementioned polymerization initiator is preferably a radical polymerization initiator for example, α,α'-azoisobutyronitrile, 2,2'-azobis-2,4-dimethylvarelonitrile, 2,2'-azobismethylisobutylate and the like. Among them, 2,2'-azobismethylisobutylate is preferably used from a viewpoint that a high molecular weight of water-soluble copolymer having alkyl-modified carboxyl groups can be obtained.

The amount of the polymerization initiator to be used is desirably 0.00003-0.002 moles with respect to 1 mole of (meth)acrylic acid. When the amount of the polymerization initiator is less than 0.00003 moles, it is possible that polymerization reaction rate is slow to be not economic. When the amount of the polymerization initiator is more than 0.002 moles, it is possible that polymerization progresses rapidly to make reaction control difficult.

The reaction temperature is preferably 50-90° C., more preferably 55-75° C. When the reaction temperature is lower than 50° C., it is possible that the viscosity of the reaction solution increases to make uniformly-stirring difficult. When the reaction temperature is above 90° C., it is possible that polymerization progresses rapidly to make reaction control difficult.

The reaction time, which depends on the reaction temperature, is usually 0.5-5 hours.

The water-soluble copolymer having alkyl-modified carboxyl groups of the present invention may be obtained by heating the reaction solution for example at 80-130° C. after completion of the reaction to evaporate the solvent. When the heating temperature is lower than 80° C., it is possible that it takes long time to evaporate the solvent. When the heating temperature is above 130° C., it is possible that water-solubility of the obtained water-soluble copolymer having alkyl-modified carboxyl groups deteriorates.

The water-soluble copolymer having alkyl-modified carboxyl groups thus obtained is characterized in that a 1 weight %-neutralized viscous liquid obtained from the copolymer shows a viscosity of 1000 mPa·s or lower and a transmittance of 95% or higher, and when 1-7 parts by weight of sodium chloride is added to 100 parts by weight of the neutralized viscous liquid, the liquid shows a highest viscosity of 10000-30000 mPa·s and a transmittance of 95% or higher. Usually, a liquid is considered to be significantly transparent when a transmittance is 95% or higher.

In viscosity measurements, 1 weight %-neutralized viscous liquids having with a pH of 6.5-7.5, which is formed by dissolving a predetermined amount of the water-soluble copolymers to an appropriate amount of pure water with stirring and adding a predetermined concentration of sodium hydroxide or, if required, electrolyte-added solutions prepared by adding a predetermined amount of sodium chloride and stirring are used as evaluation samples after standing for one hour.

Viscosity is measured at 25° C. after one minute rotating at a rotational speed of 20 rpm by using a BH type rotational viscometer with a spindle rotor No. 6.

In the present invention, a transmittance is measured at a wavelength of 425 nm in a cell with a light path length of 1 cm after degassed a sample by centrifuging.

For example, neutralized viscous liquids which has a pH of 6.5-7.5 and contains the water-soluble copolymer having alkyl-modified carboxyl groups according to the present invention at about 1 weight % may be used as a thickening agent for cosmetics and the like, wherein the neutralized viscous liquids are formed by dissolving the copolymer to pure water such as deionized water and neutralizing with alkali.

Alkalis used to neutralize the copolymer solution are not particularly limited but include alkali metal hydroxides such as sodium hydroxide, amines such as triethanolamine, diisopropanolamine, and the like. Among them, sodium hydroxide is preferably used.

The neutralized viscous liquids obtained from the water-soluble copolymer having alkyl-modified carboxyl groups according to the present invention have a very low viscosity when no electrolyte exists and have a greatly increased viscosity when electrolytes are added. Further, the neutralized viscous liquids have a sufficiently high viscosity and a very high transmittance and have moist textures without stickiness even in the presence of a relatively high concentration of electrolytes.

It is not clearly understood why the water-soluble copolymer having alkyl-modified carboxyl groups according to the present invention shows the above property. However, it is presumed that by using a specific amount of lauryl (meth)acrylate, the lauryl groups introduced into the water-soluble copolymer having alkyl-modified carboxyl groups associate with each other in an aqueous solution via hydrophobic interaction to increase viscosity and thereby effects of electrolytes change.

Accordingly, use of the water-soluble copolymer having alkyl-modified carboxyl groups according to the present invention allows manufacturing cosmetics very excellent in transparency and having moist texture without stickiness regardless of a relatively high concentration of various electrolytes as additives.

Such cosmetics include, for example, lotion, emulsion, serum, cream, cream pack, massage cream, cleansing cream, cleansing gel, cleansing foam, sunscreen, styling gel, eyeliner, mascara, lipstick, foundation and the like.

In addition, due to a low viscosity in the absence of electrolytes, those thickening agents are very useful from a viewpoint of manufacturing efficiency for cosmetics and the like. That is, since a viscosity of a solution may be maintained to low in a variety of manufacturing processes before adding electrolytes, working efficiencies in a reaction process, a transfer process, a heating process, a compounding process and the like before adding electrolytes may be greatly improved by leaving a process for adding electrolytes later.

Effect of the Invention

The present invention provides a water-soluble copolymer having alkyl-modified carboxyl groups which is able to produce a neutralized viscous liquid in which although its viscosity is very low when no electrolyte exists, the viscosity greatly increases when electrolytes are added, which has a sufficiently high viscosity and which has a very high transmittance and moist textures without stickiness even in the presence of a relatively high concentration of electrolytes.

DETAILED DESCRIPTION OF THE INVENTION

The present invention will be specifically explained below by referring to the following Examples, Comparative Examples and Referential Examples. However, the present invention is never limited by those examples.

Example 1

Into a 500 mL-four necked flask equipped with a stirrer, a thermometer, a nitrogen blowing tube and a condenser, were placed 45 g (0.625 moles) of acrylic acid; 2.7 g of lauryl methacrylate; 150 g of normal hexane and 0.081 g (0.00035 moles) of 2,2'-azobismethylisobtylate. The mixture was stirred and mixed uniformly followed by blowing a nitrogen gas into the solution in order to remove oxygen existing in the upper room of the reactor vessel, the raw materials and the solvent. Then, a reaction was conducted for 4 hours at 60-65° C. under a nitrogen atmosphere. After the reaction completed, the formed slurry was heated at 90° C. to evaporate normal hexane and, further, the resultant was dried under reduced pressure at 10 mmHg at 110° C. for 8 hours to obtain 45 g of the water-soluble copolymer having alkyl-modified carboxyl groups as white fine powder.

Example 2

The manner in Example 1 was followed but the amount of lauryl methacrylate was changed to 4.1 g to obtain 46 g of the water-soluble copolymer having alkyl-modified carboxyl groups as white fine powder.

Example 3

The manner in Example 1 was followed but 0.02 g of pentaerythritol allyl ether was added in addition to 45 g (0.625 moles) of acrylic acid, 2.7 g of lauryl methacrylate, 150 g of normal hexane and 0.081 g (0.00035 moles) of 2,2'-azobismethylisobtylate to obtain 45 g of the water-soluble copolymer having alkyl-modified carboxyl groups as white fine powder.

Example 4

The manner in Example 3 was followed but the amount of lauryl methacrylate was changed to 4.1 g to obtain 46 g of the water-soluble copolymer having alkyl-modified carboxyl groups as white fine powder.

Comparative Example 1

The manner in Example 1 was followed but the amount of lauryl methacrylate was changed to 1.8 g to obtain 44 g of the water-soluble copolymer having alkyl-modified carboxyl groups as white fine powder.

Comparative Example 2

The manner in Example 1 was followed but the amount of lauryl methacrylate was changed to 5.4 g to obtain 47 g of the water-soluble copolymer having alkyl-modified carboxyl groups as white fine powder.

Comparative Example 3

The manner in Example 3 was followed but the amount of pentaerythritol allyl ether was changed to 0.13 g to obtain 45 g of the water-soluble copolymer having alkyl-modified carboxyl groups as white fine powder.

Comparative Example 4

The manner in Example 3 was followed but 4.1 g of stearyl methacrylate was used in place of 2.7 g of lauryl methacrylate to obtain 47 g of the water-soluble copolymer having alkyl-modified carboxyl groups as white fine powder.

Comparative Example 5

The manner in Example 3 was followed but 0.9 of stearyl methacrylate was used in place of 2.7 g of lauryl methacrylate and the amount of pentaerythritol allyl ether was changed to 0.09 g from 0.02 g to obtain 44 g of the water-soluble copolymer having alkyl-modified carboxyl groups as white fine powder.

Main raw materials and their amounts used in Examples 1-4 and Comparative Examples 1-5 are summarized in Tables 1 and 2.

TABLE 1

| Main raw material | Ex. 1 | Ex. 2 | Ex. 3 | Ex. 4 |
|---|---|---|---|---|
| acrylic acid [g] | 45 (100) | 45 (100) | 45 (100) | 45 (100) |
| lauryl methacrylate [g] | 2.7 (6) | 4.1 (9.1) | 2.7 (6) | 4.1 (9.1) |
| pentaerythritol allyl ether [g] | — | — | 0.02 (0.044) | 0.02 (0.044) |

The numerical number in a parenthesis indicates an amount of the respective raw materials in parts by weight with assuming the amount of the acrylic acid used as 100 parts by weight.

TABLE 2

| Main raw material | Comp. Ex. 1 | Comp. Ex. 2 | Comp. Ex. 3 | Comp. Ex. 4 | Comp. Ex. 5 |
|---|---|---|---|---|---|
| acrylic acid [g] | 45 (100) | 45 (100) | 45 (100) | 45 (100) | 45 (100) |
| lauryl methacrylate [g] | 1.8 (4) | 5.4 (12) | 2.7 (6) | — | — |
| stearyl methacrylate [g] | — | — | — | 4.1 (9.1) | 0.9 (2) |

TABLE 2-continued

| Main raw material | Comp. Ex. 1 | Comp. Ex. 2 | Comp. Ex. 3 | Comp. Ex. 4 | Comp. Ex. 5 |
|---|---|---|---|---|---|
| pentaerythritol allyl ether [g] | — | — | 0.13 (0.29) | 0.02 (0.044) | 0.09 (0.2) |

The numerical number in a parenthesis indicates an amount of the respective raw materials in parts by weight with assuming the amount of the acrylic acid used as 100 parts by weight.

Evaluations

In order to evaluate properties as a thickening agent of water-soluble copolymers having alkyl-modified carboxyl groups obtained in Examples 1-4 and Comparative Example 1-5, viscosity and transmittance measurements were carried out regarding 1 weight %-neutralized viscous liquids of respective copolymers and electrolyte-added solutions prepared by adding sodium chloride to the liquids and mixing. Further, among these electrolyte-added solutions, those showing the highest viscosity were subjected to a moisture sensory test.

(1) Preparation of Evaluation Samples

Three grams of each of the water-soluble copolymers having alkyl-modified carboxyl groups obtained in Example 1-4 and Comparative Examples 1-5 was gradually added and dissolved to 280 g of pure water (deionized water) with stirring. To the solution was added 17 g of 6 weight %-sodium hydroxide to form 1 weight %-neutralized viscous liquids with a pH of 6.5-7.5. In addition, 1-7 weight %-electrolyte-added solutions were prepared by adding 3 g, 6 g, 9 g, 12 g, 15 g, 18 g, or 21 g of sodium chloride to 300 g of 1 weight %-neutralized viscous liquids obtained according to the manner as the same as above in order to evaluate properties of these neutralized viscous liquids in the presence of electrolytes.

In the following evaluations, these 1 weight %-neutralized viscous liquids and the various weight %-electrolyte-added solutions were used as evaluation samples after standing for one hour.

(2) Viscosity Measurement

With respect to each of the evaluation samples, viscosity was measured at 25° C. after one minute rotating at a rotational speed of 20 rpm by using a BH type rotational viscometer with a spindle rotor No. 6. Measurement results are shown in Tables 3-7.

(3) Transmittance Measurement

With respect to each of the evaluation samples, a transmittance was measured at a wavelength of 425 nm in a cell with a light path length of 1 cm after degassed by centrifuging at 2000 rpm for 30 minutes. Usually, a liquid is considered to be very transparent by visual observation when a transmittance is 95% or higher. Measurement results are shown in Tables 3-7.

(4) Sensory Evaluation On Texture

Respective evaluation samples which exhibited the highest viscosity in viscosity measurements with respect to each of the water-soluble copolymers having alkyl-modified carboxyl groups obtained in Examples 1-4 and Comparative Examples 1-5 were applied on skins of panelists consisting of 5 men and 5 women. Texture was evaluated based on feeling when the sample was spread with fingers.

Evaluation criteria are as follows:
A: moisture
B: relatively moisture
C: no impression
D: sticky Additionally, when 70% or more of the panelists score "A: moisture" or "B: relatively moisture" to a sample, the sample is considered to show moisture texture. The evaluation results are shown in Tables 8-9.

TABLE 3

| Amount of NaCl added [g] | Ex. 1 | | | Ex. 2 | | |
|---|---|---|---|---|---|---|
| | Viscosity [mPa·s] | Transmittance [%] | Remarks | Viscosity [mPa·s] | Transmittance [%] | Remarks |
| 0 | 110 | 99 | | 250 | 99 | |
| 3 | 4310 | 98 | | 25000 | 97 | Sample for S.E. |
| 6 | 17000 | 97 | | 14250 | 96 | |
| 9 | 18700 | 98 | Sample for S.E. | 7100 | 95 | |
| 12 | 14100 | 96 | | 4000 | 94 | |
| 15 | 9700 | 96 | | 2250 | 92 | |
| 18 | 5500 | 94 | | 1800 | 91 | |
| 21 | 1600 | 92 | | 1500 | 90 | |

* S.E.: Sensory Evaluation
* phase sep.: phase separation

TABLE 4

| Amount of NaCl added [g] | Ex. 3 | | | Ex. 4 | | |
|---|---|---|---|---|---|---|
| | Viscosity [mPa·s] | Transmittance [%] | Remarks | Viscosity [mPa·s] | Transmittance [%] | Remarks |
| 0 | 240 | 99 | | 300 | 99 | |
| 3 | 2940 | 98 | | 26500 | 98 | Sample for S.E. |
| 6 | 16750 | 98 | | 15000 | 97 | |
| 9 | 19300 | 96 | Sample for S.E. | 6900 | 92 | |
| 12 | 15000 | 95 | | 4500 | 94 | |
| 15 | 10450 | 94 | | 2000 | 91 | |
| 18 | 7650 | 92 | | 1900 | 91 | |
| 21 | 3760 | 90 | | 1200 | 90 | |

* S.E.: Sensory Evaluation
* phase sep.: phase separation

TABLE 5

| Amount of NaCl added [g] | Comp. Ex. 1 | | | Comp. Ex. 2 | | |
|---|---|---|---|---|---|---|
| | Viscosity [mPa·s] | Transmittance [%] | Remarks | Viscosity [mPa·s] | Transmittance [%] | Remarks |
| 0 | 188 | 99 | | 340 | 97 | |
| 3 | 44 | 98 | | 18550 | 84 | Sample for S.E. |
| 6 | 106 | 98 | | 4340 | 57 | |
| 9 | 776 | 96 | | 2900 | 34 | |
| 12 | 2990 | 95 | | 800 | 8 | |
| 15 | 4800 | 94 | | — | — | phase sep. |
| 18 | 8000 | 92 | Sample for S.E. | — | — | phase sep. |
| 21 | 7250 | 90 | | — | — | phase sep. |

* S.E.: Sensory Evaluation
* phase sep.: phase separation

TABLE 6

| Amount of NaCl added [g] | Comp. Ex. 3 | | | Comp. Ex. 4 | | |
|---|---|---|---|---|---|---|
| | Viscosity [mPa·s] | Transmittance [%] | Remarks | Viscosity [mPa·s] | Transmittance [%] | Remarks |
| 0 | 5700 | 96 | | 15200 | 97 | Sample for S.E. |
| 3 | 7100 | 88 | Sample for S.E. | 6800 | 56 | |
| 6 | 4900 | 65 | | 250 | 14 | |
| 9 | 2200 | 13 | | — | — | phase sep. |
| 12 | 50 | 2 | | — | — | phase sep. |
| 15 | — | — | phase sep. | — | — | phase sep. |
| 18 | — | — | phase sep. | — | — | phase sep. |
| 21 | — | — | phase sep. | — | — | phase sep. |

\* S.E.: Sensory Evaluation
\* phase sep.: phase separation

TABLE 7

| Amount of NaCl added [g] | Comp. Ex. 5 | | |
|---|---|---|---|
| | Viscosity [mPa·s] | Transmittance [%] | Remarks |
| 0 | 6800 | 95 | |
| 3 | 9550 | 87 | Sample for S.E. |
| 6 | 6150 | 63 | |
| 9 | 1700 | 13 | |
| 12 | 400 | 4 | |
| 15 | — | — | phase sep. |
| 18 | — | — | phase sep. |
| 21 | — | — | phase sep. |

\* S.E.: Sensory Evaluation
\* phase sep.: phase separation

TABLE 8

| Criteria | Ex. 1 [people] | Ex. 2 [people] | Ex. 3 [people] | Ex. 4 [people] |
|---|---|---|---|---|
| A | 9 | 0 | 7 | 1 |
| B | 1 | 8 | 2 | 7 |
| C | 0 | 2 | 1 | 2 |
| D | 0 | 0 | 0 | 0 |

TABLE 9

| Criteria | Comp. Ex. 1 [people] | Comp. Ex. 2 [people] | Comp. Ex. 3 [people] | Comp. Ex. 4 [people] | Comp. Ex. 5 [people] |
|---|---|---|---|---|---|
| A | 8 | 8 | 8 | 1 | 7 |
| B | 2 | 1 | 1 | 0 | 2 |
| C | 0 | 1 | 1 | 1 | 1 |
| D | 0 | 0 | 0 | 8 | 0 |

From Tables 3-9, it is understood that the water-soluble copolymers having alkyl-modified carboxyl groups obtained in Examples 1-4 produced a neutralized viscous liquid in which although its viscosity is very low when no electrolyte exists, the viscosity greatly increases when electrolytes are added, which has a sufficiently high viscosity and a very high transmittance and which has moist textures without stickiness even in the presence of a relatively high concentration of electrolytes.

Thus, it is demonstrated that the water-soluble copolymers having alkyl-modified carboxyl groups obtained in Examples 1-4 can be used as a thickening agent having excellent properties as described above.

Referential Example 1

Components 1-6 shown below were added at the respective percentages and uniformly mixed by stirring. Further, components 7-10 were added and uniformly mixed by stirring and solubilized to prepare lotion.

| | | |
|---|---|---|
| 1. | Water-soluble copolymer having alkyl-modified carboxyl groups (Example 4) | 0.1% |
| 2. | Sodium hydroxide | 0.28% |
| 3. | 2-glucoside ascorbate | 2.0% |
| 4. | Citric acid | 0.01% |
| 5. | Sodium hydrogenphosphate | 0.1% |
| 6. | Distilled water | balance to 100% sum |
| 7. | Ethanol | 8.0% |
| 8. | POE(30) POP(6) decyl tetradecyl ether | 0.3% |
| 9. | Preservative | q.s. |
| 10. | Incense | q.s. |

\* q.s.: quantus sufficiat

Referential Example 2

Components 1-8 shown below were added at the respective percentages and heated at 80° C. Further, components 9-17 were added and heated at 80° C. followed by stirring to emulsify. Then, emulsion was prepared by cooling with stirring.

| | | |
|---|---|---|
| 1. | POE(20) sorbitan monostearate | 1.0% |
| 2. | POE(40) sorbitol tetraoleate | 1.5% |
| 3. | Lipophilic glyceryl monostearate | 1.0% |
| 4. | Stearic acid | 0.5% |
| 5. | Behenyl alcohol | 1.5% |
| 6. | Squalane | 5.0% |
| 7. | Cetyl 2-ethylhexanoate | 5.0% |
| 8. | Methyl polysiloxane | 0.5% |
| 9. | Water-soluble copolymer having alkyl-modified carboxyl groups (Example 2) | 0.1% |
| 10. | Xanthan gum | 0.1% |
| 11. | Sodium hydroxide | 0.05% |
| 12. | Sodium lactate | 1.0% |
| 13. | Citric acid | 0.01% |
| 14. | Sodium hydrogenphosphate | 0.1% |
| 15. | 1,3-butylene glycol | 7.0% |
| 16. | Preservative | q.s. |
| 17. | Distilled water | balance to 100% sum |

\* q.s.: quantus sufficiat

Referential Example 3

Components 1-11 shown below were added at the respective percentages and dissolved at room temperature to form a viscous liquid. Then, serum was prepared.

| | |
|---|---|
| 1. Water-soluble copolymer having alkyl-modified carboxyl groups (Example 1) | 0.2% |
| 2. Sodium hydroxide | 0.08% |
| 3. L-ascorbyl magnesium phosphate | 3.0% |
| 4. Sodium Citrate | 0.5% |
| 5. Tetrasodium EDTA | 0.1% |
| 6. 1,3-butylene glycol | 7.0% |
| 7. Glycerin | 8.0% |
| 8. Distilled water | balance to 100% sum |
| 9. Cosmetic component | q.s. |
| 10. Preservative | q.s. |
| 11. Ethanol | 5.0% |

* q.s.: quantus sufficiat

Referential Example 4

Components 1-6 shown below were added at the respective percentages and headed at 80° C. Further, components 7-14 were added at the respective percentages, heated at 80° C., and stirred to emulsify. Then, cream was prepared by cooling with stirring.

| | |
|---|---|
| 1. Decaglyceryl pentaoleate | 3.0% |
| 2. Beewax | 2.0% |
| 3. Cetanol | 2.0% |
| 4. Squalane | 5.0% |
| 5. Glyceryl tri-2-ethylhexanoate | 2.0% |
| 6. Methyl polysiloxane | 0.5% |
| 7. Glycerin | 5.0% |
| 8. L-ascorbyl magnesium phosphate | 3.0% |
| 9. Sodium citrate | 0.5% |
| 10. Tetrasodium EDTA | 0.1% |
| 11. Water-soluble copolymer having alkyl-modified carboxyl groups (Example 3) | 0.15% |
| 12. Sodium hydroxide | 0.06% |
| 13. Preservative | q.s. |
| 14. Distilled water | balance to 100% sum |

* q.s.: quantus sufficiat

Referential Example 5

Components 1-4 shown below were added at the respective percentages and headed at 80° C. Further, components 5-12 were added at the respective percentages, heated at 80° C., and stirred to emulsify. Then, cream pack was prepared by cooling with stirring.

| | |
|---|---|
| 1. POE(20) POP(4) cetyl ether | 0.8% |
| 2. Diglyceryl monostearate | 0.2% |
| 3. Glyceryl tri-2-ethylhexanoate | 1.0% |
| 4. Meduhome oil | 1.0% |
| 5. Glycerin | 5.0% |
| 6. 1,3-butylene glycol | 3.0% |
| 7. Water-soluble copolymer having alkyl-modified carboxyl groups (Example 2) | 0.1% |
| 8. Sodium hydroxide | 0.28% |
| 9. Hydroxyethyl cellulose | 0.3% |
| 10. 2-Glucoside ascorbate | 2.0% |
| 11. Preservative | q.s. |
| 12. Distilled water | balance to 100% sum |

* q.s.: quantus sufficiat

Referential Example 6

Components 1-7 shown below were added at the respective percentages and headed at 80° C. Further, components 8-13 were added at the respective percentages, heated at 80° C., and stirred to emulsify. Then, massage cream was prepared by cooling with stirring.

| | |
|---|---|
| 1. POE(20) cetyl ether | 2.0% |
| 2. Lipophilic glyceryl monostearate | 4.0% |
| 3. Cetanol | 2.0% |
| 4. White vaseline | 6.0% |
| 5. Squalane | 30.0% |
| 6. Glyceryl tri-2-ethylhexanoate | 5.0% |
| 7. Methyl polysiloxane | 0.5% |
| 8. Water-soluble copolymer having alkyl-modified carboxyl groups (Example 4) | 0.1% |
| 9. Sodium hydroxide | 0.04% |
| 10. Glycerin | 5.0% |
| 11. Sodium PCA | 1.0% |
| 12. Preservative | q.s. |
| 13. Distilled water | balance to 100% sum |

* q.s.: quantus sufficiat

Referential Example 7

Components 1-7 shown below were added at the respective percentages and heated at 80° C. Further, components 8-13 were added at the respective percentages, heated at 80° C., stirred to emulsify. Then, cleansing cream was prepared by cooling with stirring.

| | |
|---|---|
| 1. POE(20) sorbitan monostearate | 2.0% |
| 2. POE(40) sorbitol tetraoleate | 1.0% |
| 3. Self-emulsifying glyceryl monostearate | 2.0% |
| 4. Stearic acid | 4.0% |
| 5. Cetanol | 2.0% |
| 6. Liquid paraffin | 30.0% |
| 7. Glyceryl tri-2-ethylhexanoate | 10.0% |
| 8. 1,3-butylene glycol | 5.0% |
| 9. Water-soluble copolymer having alkyl-modified carboxyl groups (Example 2) | 0.1% |
| 10. Sodium hydroxide | 0.04% |
| 11. L-serine | 1.0% |
| 12. Preservative | q.s. |
| 13. Distilled water | balance to 100% sum |

* q.s.: quantus sufficiat

Referential Example 8

Components 1-10 shown below were added at the respective percentages and uniformly mixed at room temperature to form gel. Then, cleansing gel was prepared.

| | |
|---|---|
| 1. AQUPEC HV-501E (carboxyvinyl polymer) | 0.1% |
| 2. Water-soluble copolymer having alkyl-modified carboxyl groups (Example 1) | 0.1% |
| 3. Sodium hydroxide | 0.08% |
| 4. Sodium PCA | 1.0% |
| 5. Hydroxypropyl cellulose | 0.5% |
| 6. POE(30) cetyl ether | 16.0% |
| 7. POE(5) lauryl ether | 12.0% |

-continued

| | | |
|---|---|---|
| 8. 1,3-butylene glycol | 10.0% | |
| 9. Distilled water | balance to 100% sum | |
| 10. Preservative | q.s. | |

* q.s.: quantus sufficiat

Referential Example 9

Components 1-8 shown below were added at the respective percentages and heated at 80° C. Further, components 9-14 were added at the respective percentages, heated at 80° C. and mixed. Then, cleansing foam was prepared by cooling with stirring.

| | | |
|---|---|---|
| 1. Myristic acid | 15.0% | |
| 2. Palmitic acid | 5.0% | |
| 3. Stearic acid | 3.0% | |
| 4. Beewax | 3.0% | |
| 5. Polyethylene glycol 6000 | 2.0% | |
| 6. Ethylene glycol distearate | 2.0% | |
| 7. Diethanolamide cocoate | 3.0% | |
| 8. Concentrated glycerin | 15.0% | |
| 9. Water-soluble copolymer having alkyl-modified carboxyl groups (Example 3) | 0.1% | |
| 10. Sodium hydroxide | 0.04% | |
| 11. Potassium hydroxide | 5.5% | |
| 12. Sodium PCA | 0.5% | |
| 13. Sodium N-lauroylsarcosine | 10.0% | |
| 14. Distilled Water | balance to 100% sum | |

Referential Example 10

Components 1-10 shown below were added at the respective percentages and heated at 80° C. Further, components 11-16 were added at the respective percentages, heated at 80° C. and stirred to emulsify. Then, sunscreen was prepared by cooling with stirring.

| | |
|---|---|
| 1. Water-soluble copolymer having alkyl-modified carboxyl groups (Example 4) | 0.1% |
| 2. Sodium carboxymethylcellulose | 0.3% |
| 3. Sodium hydroxide | 0.28% |
| 4. 2-glucoside ascorbiate | 2.0% |
| 5. Citric acid | 0.01% |
| 6. Sodium hydrogenphosphate | 0.1% |
| 7. Preservative | q.s. |
| 8. 1,3-butylene glycol | 7.0% |
| 9. Glycerin | 8.0% |
| 10. Distilled water | balance to 100% sum |
| 11. Sorbitan monostearate | 0.5% |
| 12. Polyoxyethylene sorbitan POE(20) monooleate | 0.5% |
| 13. Sorbitan sesquioleate | 0.5% |
| 14. Cetanol | 2.0% |
| 15. 2-ethylhexyl paramethoxycinnamate | 10.0% |
| 16. Ethanol | 10.0% |

* q.s.: quantus sufficiat

Referential Example 11

Components 1-6 shown below were added at the respective percentages and dissolved at room temperature. Then, styling gel was prepared by stirring to uniformly mix.

| | |
|---|---|
| 1. AQUPEC HV-505E (carboxyvinyl polymer) | 0.1% |
| 2. Water-soluble copolymer having alkyl-modified carboxyl groups (Example 3) | 0.1% |
| 3. Sodium hydroxide | 0.08% |
| 4. Vinylpyrrolidone-vinyl acetate copolymer solution (H) (*1) | 10.0% |
| 5. Sodium PCA | 1.0% |
| 6. Distilled water | balance to 100% sum |

(*1): PVP/VAE-735 manufactured by ISP Corporation

Referential Example 12

Components 1-9 shown below were added at the respective percentages and dissolved at room temperature. Then, eyeliner was prepared by stirring to uniformly mix.

| | |
|---|---|
| 1. Alkyl acrylate copolymer emulsion (*2) | 30.0% |
| 2. 1,3-butylene glycol | 15.0% |
| 3. Black iron oxide | 15.0% |
| 4. Water-soluble copolymer having alkyl-modified carboxyl groups (Example 1) | 0.1% |
| 5. Sodium hydroxide | 0.04% |
| 6. Sodium carboxymethylcellulose | 2.0% |
| 7. Sodium chloride | 0.5% |
| 8. Preservative | q.s. |
| 9. Distilled water | balance to 100% sum |

* q.s.: quantus sufficiat
(*2): YODOSOL GH810 manufactured by Nippon NSC Ltd.

Referential Example 13

Components 1-10 shown below were added at the respective percentages and heated at 80° C. Further, components 11-16 were added at the respective percentages, heated at 80° C. and stirred to emulsify. Then, mascara was prepared by cooling with stirring.

| | |
|---|---|
| 1. Stearic acid | 2.0% |
| 2. Carnauba wax | 2.0% |
| 3. Beewax | 3.0% |
| 4. Polyoxyethylene sorbitan POE(20) monooleate | 1.0% |
| 5. Sorbitan sesquioleate | 0.5% |
| 6. Alkyl acrylate copolymer emulsion (*2) | 1.0% |
| 7. Triethanolamine | 1.1% |
| 8. Propylene glycol | 1.0% |
| 9. Black iron oxide | 10.0% |
| 10. Kaolin | 10.0% |
| 11. Water-soluble copolymer having alkyl-modified carboxyl groups (Example 1) | 0.2% |
| 12. Sodium hydroxide | 0.08% |
| 13. Sodium carboxymethylcellulose | 2.5% |
| 14. Sodium chloride | 0.1% |
| 15. Preservative | q.s. |
| 16. Distilled water | balance to 100% sum |

* q.s.: quantus sufficiat
(*2): YODOSOL GH810 manufactured by Nippon NSC Ltd.

Referential Example 14

Components 1-11 shown below were added at the respective percentages and dispersed by roll milling. The resultant was run into a mold at a high temperature. Then, lipstick was prepared by filling the cooled and molded product into a container.

|  |  |
|---|---|
| 1. Candelilla wax | 5.0% |
| 2. Ceresin | 5.0% |
| 3. Carnauba wax | 3.0% |
| 4. Microcrystalline wax | 3.0% |
| 5. Glyceryl tri-2-ethylhexanoate | 20.0% |
| 6. Isotridecyl isononanoate | 20.0% |
| 7. Diisostearyl maleate | balance to 100% sum |
| 8. Water-soluble copolymer having alkyl-modified carboxyl groups (Example 4) | 1.0% |
| 9. Silicic anhydride | 1.0% |
| 10. Coloring agent | q.s. |
| 11. Preservative | q.s. |

* q.s.: quantus sufficiat

Referential Example 15

Components 1-11 shown below were added at the respective percentages and heated at 80° C. Further, components 12-17 were added at the respective percentages, heated at 80° C. and mixed. Then, foundation was prepared by cooling with stirring.

|  |  |
|---|---|
| 1. Lipophilic glyceryl monostearate | 1.0% |
| 2. Stearic acid | 5.0% |
| 3. Behenyl alcohol | 1.0% |
| 4. Cetanol | 0.5% |
| 5. Squalane | 5.0% |
| 6. Titanium oxide | 4.0% |
| 7. Red iron oxide | q.s. |
| 8. Yellow iron oxide | q.s. |
| 9. Black iron oxide | q.s. |
| 10. Talc | 4.0% |
| 11. Soy bean phospholipid | 0.3% |
| 12. 1,3-butylene glycol | 8.0% |
| 13. Triethanolamine | 1.5% |
| 14. Water-soluble copolymer having alkyl-modified carboxyl groups (Example 4) | 0.2% |
| 15. Sodium hydroxide | 0.08% |
| 16. Sodium PCA | 1.0% |
| 17. Distilled water | balance to 100% sum |

* q.s.: quantus sufficiat

The cosmetics which use the water-soluble copolymer having alkyl-modified carboxyl groups obtained in Examples 1-4 showed moisture texture without stickiness. In addition, cosmetics and the like containing electrolytes and the like showed similar properties.

What we claimed is:

1. A water-soluble copolymer having alkyl-modified carboxyl groups obtained by
    polymerizing 100 parts by weight of (meth)acrylic acid, 5-10 parts by weight of lauryl(meth)acrylate, and 0.001-0.044 parts by weight of a compound having two or more of ethylenic unsaturated groups,
    wherein a liquid containing 1 weight % of said water-soluble copolymer having alkyl-modified carboxyl groups has a viscosity of 1000 mPa·s or lower and a transmittance of 95% or higher, and
    when 1-7 parts by weight of sodium chloride is added to 100 parts by weight of the liquid containing 1 weight % of said water-soluble copolymer having alkyl-modified carboxyl groups, a viscosity is 10000-30000 mPa·s and a transmittance is 95% or higher.

2. The water-soluble copolymer having alkyl-modified carboxyl groups according to claim 1, wherein the compound having two or more of ethylenic unsaturated groups is at least one selected from a group consisting of pentaerythritol allyl ether, diethylene glycol diallyl ether, polyethylene glycol diallyl ether and polyallyl saccharose.

3. A thickening agent comprising the water-soluble copolymer having alkyl-modified carboxyl groups according to claim 1 or 2.

4. The water-soluble copolymer having alkyl-modified carboxyl groups according to claim 1, wherein the liquid containing 1 weight % of said water-soluble copolymer having alkyl-modified carboxyl groups has a pH of 6.5 to 7.5.

5. The water-soluble copolymer having alkyl-modified carboxyl groups according to claim 1, wherein the liquid containing 1 weight % of said water-soluble copolymer having alkyl-modified carboxyl groups is neutralized by the addition of an alkali selected from a group consisting of sodium hydroxide, triethanolamine and diisopropanolamine.

6. The water-soluble copolymer having alkyl-modified carboxyl groups according to claim 1 present in a lotion, emulsion, serum, cream, cream pack, massage cream, cleansing cream, cleansing gel, cleansing foam, sunscreen, styling gel, eyeliner, mascara, lipstick or foundation.

* * * * *